US010414862B2

(12) United States Patent
Zhou et al.

(10) Patent No.: US 10,414,862 B2
(45) Date of Patent: *Sep. 17, 2019

(54) POLYMERIC AMINE SYNERGIST

(71) Applicant: Hewlett-Packard Development Company, L.P., Houston, TX (US)

(72) Inventors: Zhang-Lin Zhou, San Diego, CA (US); Rodney David Stramel, San Diego, CA (US); Gregg A. Lane, San Diego, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 72 days.

This patent is subject to a terminal disclaimer.

(21) Appl. No.: 15/562,858

(22) PCT Filed: Jul. 9, 2015

(86) PCT No.: PCT/US2015/039819
§ 371 (c)(1),
(2) Date: Sep. 28, 2017

(87) PCT Pub. No.: WO2017/007493
PCT Pub. Date: Jan. 12, 2017

(65) Prior Publication Data
US 2018/0112037 A1 Apr. 26, 2018

(51) Int. Cl.
*C09D 11/101* (2014.01)
*C08G 65/333* (2006.01)
*C08K 5/18* (2006.01)
*C08G 65/331* (2006.01)
*C08G 65/334* (2006.01)
*C08G 65/335* (2006.01)
*C07C 217/86* (2006.01)
*C09D 11/102* (2014.01)
*C09D 11/38* (2014.01)
*C09D 11/54* (2014.01)

(52) U.S. Cl.
CPC ...... *C08G 65/33396* (2013.01); *C07C 217/86* (2013.01); *C08G 65/3315* (2013.01); *C08G 65/3346* (2013.01); *C08G 65/3356* (2013.01); *C08G 65/33313* (2013.01); *C08K 5/18* (2013.01); *C09D 11/101* (2013.01); *C09D 11/102* (2013.01); *C09D 11/38* (2013.01); *C09D 11/54* (2013.01)

(58) Field of Classification Search
CPC ..... C09D 11/101; C09D 11/102; C09D 11/38; C09D 11/54; C08K 5/18; C08G 65/33396; C08G 65/3315; C08G 65/33313; C08G 65/3346; C08G 65/3356; C07C 217/86
See application file for complete search history.

(56) References Cited

U.S. PATENT DOCUMENTS

| 4,418,138 | A | 11/1983 | Curtis |
| 4,450,279 | A | 5/1984 | Shirosaki et al. |
| 4,459,416 | A | 7/1984 | Curtis et al. |
| 4,602,097 | A | 7/1986 | Curtis |
| 5,905,164 | A | 5/1999 | Anderson et al. |
| 5,907,046 | A | 5/1999 | Bearson et al. |
| 6,025,408 | A | 2/2000 | Williams et al. |
| 7,335,782 | B2 | 2/2008 | Herlihy et al. |
| 8,530,510 | B2* | 9/2013 | Loccufier ............... C07C 69/76 514/434 |
| 8,598,249 | B2 | 12/2013 | Noirot et al. |
| 8,946,449 | B2 | 2/2015 | Madsen et al. |
| 2004/0132862 | A1 | 7/2004 | Woudenberg |
| 2011/0195198 | A1 | 8/2011 | Loccufier et al. |
| 2013/0012611 | A1 | 1/2013 | Davidson et al. |
| 2014/0335326 | A1 | 11/2014 | Gevaert et al. |
| 2018/0072845 | A1* | 3/2018 | Zhou ....................... C08K 5/18 |

FOREIGN PATENT DOCUMENTS

| CN | 1594369 | 3/2005 |
| CN | 1594399 | 3/2005 |
| CN | 101665575 | 3/2010 |
| CN | 102250059 | 11/2011 |
| WO | WO2002040464 | 5/2002 |
| WO | WO2008061954 | 5/2008 |
| WO | WO2012003644 | 1/2012 |
| WO | WO2013146061 | 10/2013 |
| WO | WO2013146062 | 10/2013 |
| WO | WO2015010729 | 1/2015 |

OTHER PUBLICATIONS

Akat, Hakan, et al. "Poly(ethylene glycol)-Thioxanthone Prepared by Diels-Alder Click Chemistry as One-Component Polymeric Photoinitiator for Aqueous Free-Radical Polymerization"; Journal of Polymer Science: Part A: Polymer Chemistry, vol. 48, (2010) pp. 2109-2114.

Cesur et al, "Difunctional monomeric and polymeric photoinitiators: Synthesis and photoinitiating behaviors", Progress in Organic Coatings 86 (2015) 71-78.

Gilman et al., "Orientation in the 10-Thiaxanthenone Nucleus", Contribution from the Chemical Laboratory of Iowa State College, vol. 24, pp. 1914-1916, Jun. 8, 1959.

Hammick et al., "A New Synthesis of 1-Amino-4-methylthioxanthone and of Miracil D.", Journal of the Chemical Society (Resumed), Issue 0, 1952, pp. 1077-1080.

Nazir et al. "Donor-Acceptor Type Thioxanthones: Synthesis, Optical Properties, and Two-Photon Induced Polymerization" Macromolecules, American Chem. Society pp. A-G.

(Continued)

*Primary Examiner* — Sanza L. McClendon
(74) *Attorney, Agent, or Firm* — HP Inc. Patent Department

(57) ABSTRACT

A polymeric amine synergist is disclosed herein. An example of the polymeric amine synergist includes an aniline moiety, a polyethylene glycol chain, and an ether linkage attaching one end of the polyethylene glycol chain to the aniline moiety. The polymeric amine synergist may be included in a photo curable ink composition.

15 Claims, No Drawings

(56) References Cited

OTHER PUBLICATIONS

Sharp, "A New Synthesis of Lucanthone (Miracil D, Nilodin)", Journal of the Chemical Society (Resumed), Issue 0, 1951, pp. 2961-2963.
Wen et al "Amphipathic hyperbranched polymeric thioxanthone photoinitiators (AHPTXs): Synthesis, characterization and photoinitiated polymerization" Polymer50 (2009) 3917-3923.
Yin-Zhi et al "Synthesis and Crystal Structure of 2-hydroxyl-4-methyl-thioxanthone", Advanced Materials Research vols. 581-582 (2012) pp. 189-192.
International Search Report and Written Opinion for International Application No. PCT/US2015/039819 dated Oct. 30, 2015, 9 pages.

* cited by examiner

POLYMERIC AMINE SYNERGIST

BACKGROUND

Curing of ink by radiation, and in particular ultraviolet (UV) radiation curing, has become popular. UV curable inks can be cured after printing by the application of UV light. UV curable inks often include monomers that form polymers by free radical polymerization. The growing end of each polymer chain is a radical that reacts with additional monomers, transferring the radical to the end of the chain as each monomer is added. A photoinitiator may be used to form the first radicals to begin the polymerization process. As an example, the photoinitiator is capable of absorbing UV light to generate radicals to react with the monomers.

Two types of photoinitiators can be used in UV curable compositions. Type I photoinitiators are unimolecular photoinitiators that undergo a hemolytic bond cleavage upon absorption of UV light, forming radicals. Type-II photoinitiators are bimolecular photoinitiators. Type-II photoinitiators are a system that includes a photoinitiator with a synergist, which together can form radicals upon exposure to UV light. Some type-II photoinitiators react by hydrogen abstraction from the synergist to the photoinitiator.

DETAILED DESCRIPTION

The present disclosure is drawn to polymeric amine synergists. In an example, the present disclosure provides polymeric amine synergists including an aniline moiety modified with a polyethylene glycol chain connected to the aniline moiety through an ether linkage.

The polymeric amine synergists disclosed herein are generally water soluble and stable in aqueous inks, such as aqueous thermal inkjet inks. The polymeric amine synergists disclosed herein also resist migration in the ink after curing. In contrast, some small molecular weight synergists, such as methyldiethanolamine, trimethylamine, and its analogs, may have unwanted odor, toxicity, and undesirable migration in cured materials.

The inkjet printing industry uses various types of inks, such as oil-based inks, solvent-based (non-aqueous) inks, water-based (aqueous) inks, and solid inks which are melted in preparation for dispensing. Solvent-based inks are fast drying, and as a result, are widely used for industrial printing. When solvent-based inks containing binders and other ingredients are jetted onto a substrate, the solvent(s) partially or fully evaporate from the ink, leaving the binder and other ingredients, such as pigment particles, on the printed substrate in the form of a dry film. During the drying process, the solvents, which are often volatile organic compounds (VOC), emit undesirable vapors. Vapor production can increase greatly with higher printing speeds or for wide format images, where large amounts of ink are deposited onto a substrate. As a result of this and other concerns, efforts have been made to prepare water-based inks. However, radiation-curable (or photo-curable) water-based ink compositions are noticeably limited among available options due, at least in part, to their specific formulation properties. Accordingly, the development of radiation-curable water-based inks, also referred to as photo curable inks or photo curable ink compositions, that exhibit specific desirable printing properties such as, for example, jetting properties as well as improved adhesion, would be an advancement in the field of inkjet technology.

Examples of the photo curable ink composition disclosed herein are aqueous inks that include an example of the polymeric amine synergist. As mentioned above, in an example, the polymeric amine synergist includes the aniline moiety, the polyethylene glycol chain, and an ether linkage attaching one end of the polyethylene glycol chain to the aniline moiety. Each component of the polymeric amine synergist is discussed in greater detail below.

A portion of the polymeric amine synergist disclosed herein includes the aniline moiety modified with the ether linkage. As used herein, "aniline moiety" may refer to the portion of the synergist structure that includes a phenyl group attached to an amino group. The aniline moiety may be aniline (i.e., phenylamine or aminobenzene, $C_6H_5NH_2$), as well as analogs of this compound with attached R-groups, such as dimethylaniline. As such, the amino group of the aniline moiety may be a primary amine, a secondary amine, or a tertiary amine.

The other portion of the polymeric amine synergist disclosed herein includes polyethylene glycol chain(s). In an example, one end of the polyethylene glycol chain is attached to the aniline moiety through the ether linkage. The molecular weight of the polyethylene glycol chain can, in some cases, affect the solubility of the final polymeric amine synergist. For example, a higher ratio of oxygen atoms to carbon atoms in the polyethylene glycol chain tends to render the polymeric amine synergist more water soluble. The molecular weight of the polyethylene glycol chain can also affect the degree to which the polymeric amine synergist can migrate in a cured ink. Longer polyethylene glycol chains can make it more difficult for the polymeric amine synergist to move within a cured ink, thus decreasing migration. Therefore, the molecular weight and length of the polyethylene glycol chain can be selected to provide good water solubility and low migration of the polymeric amine synergist in cured ink.

As noted above, the ether linkage connects the polyethylene glycol chain to the aniline moiety. As used herein, "ether linkage" refers to the ether group (i.e., R'—O—R") that connects the benzene ring of the aniline moiety with the polyethylene glycol chain. R' and R" of the ether linkage may be part of the aniline moiety and the polyethylene glycol chain, respectively. For example, the R' of the ether linkage may be one of the carbon atoms in the benzene ring and the R" of the ether linkage may be the carbon atom at one end of the polyethylene glycol chain. It is to be understood that the ether linkage may be attached to the aniline moiety at different positions on the benzene ring. For example, the R' carbon atom of the ether linkage may be the carbon atom at the meta position or the para position relative to where the amino group is attached to the benzene ring. The position at which the ether linkage is attached depends, in part, on the starting material used as the aniline moiety when forming the polymeric amine synergist. Examples of the aniline moiety starting material that allow the ether linkage to attach at the para position include 4-aminophenol, 4-dimethylaminophenol, etc. An example of the aniline moiety stating material that allows the ether linkage to attach at the meta position is 3-aminophenol. The ether linkage can be formed by a suitable reaction, such as a substitution reaction.

In some examples, the aniline moiety, polyethylene glycol chain, and ether linkage do not form the entire polymeric amine synergist. In some examples, the polymeric amine synergist may include additional aniline moieties and/or polyethylene glycol chains. In some other examples, the polymeric amine synergist may have functional group(s) attached to an opposed end of the polyethylene glycol chain.

In one example, the polymeric amine synergist has a formula (I) of:

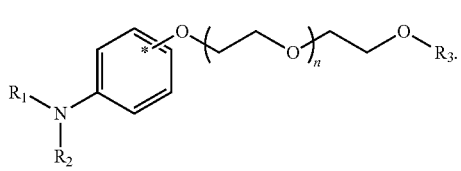

In formula (I), $R_1$, $R_2$ and $R_3$ are each independently selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, a substituted or unsubstituted aralkyl group, a halogen atom, —$NO_2$, —O—$R_d$, —CO—$R_d$, —CO—O—$R_d$, —O—CO—$R_d$, —CO—$NR_dR_e$, —$NR_dR_e$, —$NR_d$—CO—$R_e$, —$NR_d$-CO-O—$R_e$, —$NR_d$—CO—$NR_eR_f$, —$SR_d$, —SO—$R_d$, —$SO_2$—$R_d$, —$SO_2$—O—$R_d$, —$SO_2NR_dR_e$ and a perfluoroalkyl group. $R_d$, $R_e$, and $R_f$ are each independently selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, and a substituted or unsubstituted aralkyl group. Some examples of suitable alkyl groups include methyl, ethyl, propyl, isopropyl, butyl, isobutyl, pentyl, hexyl, etc. One example of a suitable alkene group is an ethylene group. Some examples of suitable aryl groups include phenyl, phenylmethyl, etc. In formula (I), the polyethylene glycol chain has n number of repeating monomer units, where n ranges from 1 to 200.

In another example, the polymeric amine synergist includes an additional aniline moiety attached to the opposed end of the polyethylene glycol chain through an additional ether linkage. In this example, the polymeric amine synergist has the formula (II) of:

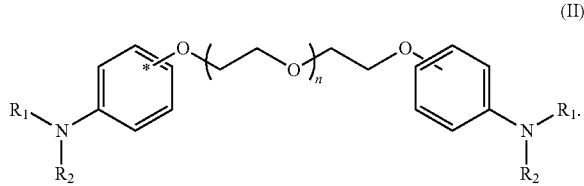

In formula (II), $R_1$ and $R_2$ are each independently selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, a substituted or unsubstituted aralkyl group, a halogen atom, —$NO_2$, —O—$R_d$, —CO—$R_d$, —CO—O—$R_d$, —O—CO—$R_d$, —CO—$NR_dR_e$, —$NR_dR_e$, —$NR_d$—CO—$R_e$, —$NR_d$—CO—O—$R_e$, —$NR_d$—CO—$NR_eR_f$, —$SR_d$, —SO—$R_d$, —$SO_2$—$R_d$, —$SO_2$—O—$R_d$, —$SO_2NR_dR_e$ and a perfluoroalkyl group. $R_d$, $R_e$, and $R_f$ are each independently selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, and a substituted or unsubstituted aralkyl group. As mentioned above, some examples of suitable alkyl groups include methyl, ethyl, propyl, isopropyl, butyl, isobutyl, pentyl, hexyl, etc.; an example of a suitable alkene group is an ethylene group; and some examples of suitable aryl groups include phenyl, phenylmethyl, etc. It is to be understood that these groups may be used in any of the formulas disclosed herein. In formula (I), the polyethylene glycol chain has n number of repeating monomer units, where n ranges from 1 to 200.

In yet another example, the polymeric amine synergist includes first, second, and third aniline moieties. Additionally, in this example, the first, second, and third aniline moieties are each individually and respectively attached to first, second, and third ether linkages. The first, second, and third ether linkages are attached to first, second, and third polyethylene glycol chains, respectively. In an example, the first ether linkage attaches one end of the first polyethylene glycol chain to the first aniline moiety. The opposed end of the first polyethylene glycol chain is attached to each of the second and third polyethylene glycol chains through carbon atom(s). An example of the polymeric amine synergist having three aniline moieties has the following formula (III) of:

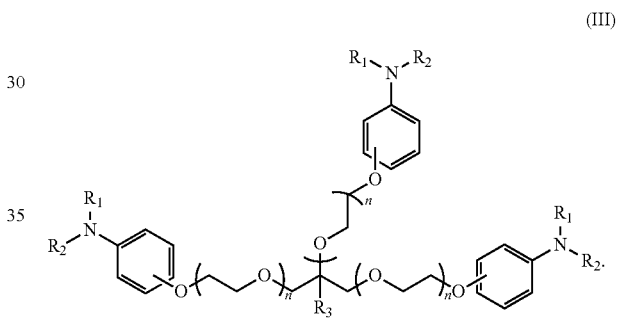

In formula (III), $R_1$, $R_2$ and $R_3$ are each independently selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, a substituted or unsubstituted aralkyl group, a halogen atom, —$NO_2$, —O—$R_d$, —CO—$R_d$, —CO—O—$R_d$, —O—CO—$R_d$, —CO—$NR_dR_e$, —$NR_dR_e$, —$NR_d$—CO—$R_e$, —$NR_d$—CO—O—$R_e$, —$NR_d$—CO—$NR_eR_f$, —$SR_d$, —SO—$R_d$, —$SO_2$—$R_d$, —$SO_2$—O—$R_d$, —$SO_2NR_dR_e$ and a perfluoroalkyl group. $R_d$, $R_e$, and $R_f$ are each independently selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, and a substituted or unsubstituted aralkyl group. As mentioned above, some examples of suitable alkyl groups include methyl, ethyl, propyl, isopropyl, butyl, isobutyl, pentyl, hexyl, etc.; one example of a suitable alkene group is an ethylene group; and some examples of suitable aryl groups include phenyl, phenylmethyl, etc. In formula (III), the first, second, and third polyethylene glycol chains have n number of repeating monomer units, where n ranges from 1 to 200.

Still further, in another example, the polymeric amine synergist includes first, second, third, and fourth aniline moieties. In this example, the first, second, third, and fourth aniline moieties are each individually and respectively attached to first, second, third, and fourth ether linkages. The first, second, third, and fourth ether linkages are attached to first, second, third, and fourth polyethylene glycol chains, respectively. In an example, the first ether linkage attaches one end of the first polyethylene glycol chain to the first aniline moiety. The opposed end of the first polyethylene glycol chain is attached to each of the second, third, and fourth polyethylene glycol chains through carbon atom(s). An example of the polymeric amine synergist having four aniline moieties has the following formula (IV) of:

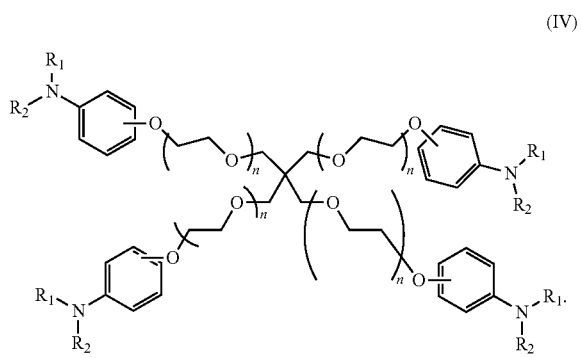

In formula (IV), $R_1$ and $R_2$ are each independently selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, a substituted or unsubstituted aralkyl group, a halogen atom, $-NO_2$, $-O-R_d$, $-CO-R_d$, $-CO-O-R_d$, $-O-CO-R_d$, $-CO-NR_dR_e$, $-NR_dR_e$, $-NR_d-CO-R_e$, $-NR_d-CO-O-R_e$, $-NR_d-CO-NR_eR_f$, $-SR_d$, $-SO-R_d$, $-SO_2-R_d$, $-SO_2-O-R_d$, $-SO_2NR_dR_e$ and a perfluoroalkyl group. $R_d$, $R_e$, and $R_f$ are each independently selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, and a substituted or unsubstituted aralkyl group. As mentioned above, some examples of suitable alkyl groups include methyl, ethyl, propyl, isopropyl, butyl, isobutyl, pentyl, hexyl, etc.; one example of a suitable alkene group is an ethylene group; and some examples of suitable aryl groups include phenyl, phenylmethyl, etc. In formula (IV), the first, second, third, and fourth polyethylene glycol chains have n number of repeating monomer units, where n ranges from 1 to 200.

In each of formulas I through IV, it is noted that the polyethylene glycol chain(s) may be connected to different positions of the benzene ring of the aniline moiety.

The molecular weight of the polymeric amine synergist can affect its degree of migration in cured ink. For example, a polymeric amine synergist with a weight average molecular weight ($M_w$) of about 500 or more can have reduced migration in cured ink compared with a small molecule synergist. Migration can be further reduced by increasing the $M_w$ of the polymeric amine synergist to about 1000 or more. In one example, the polymeric amine synergist can have a $M_w$ ranging from about 500 to about 5000. Polyethylene glycols of various molecular weights are available, allowing for the production of polymeric amine synergists with various molecular weights. In some examples, the polyethylene glycol chain can be selected from PEG 300, PEG 550, PEG 600, PEG 750, PEG 1000, and PEG 2000.

The molecular weight of the polymeric amine synergist can also be changed (in some instances minimally) by changing or adding R groups to the aniline moiety. It is noted that when referring to "R groups" generically herein, this term is defined to include at least H and organic side chain side groups (e.g., methyl, ethyl, etc.), and other specific constituents described and defined elsewhere herein, e.g., R, $R_1$, $R_2$, $R_3$, $R_4$, $R_5$, $R_6$, $R_d$, $R_e$, $R_f$, etc.

The molecular weight of the polymeric amine synergist can also affect the synergist's solubility in water. As previously described, the molecular weight of the polymeric amine synergist may be affected by the polyethylene glycol chain(s). Although the aniline moiety(ies) alone can be insoluble in water, adding the water soluble polyethylene glycol chain(s) can make the entire polymeric amine synergist water soluble. As the polyethylene glycol chain increases, the molecular weight increases, and the water solubility increase. In such cases, the soluble polyethylene glycol chain(s) can have a sufficient molecular weight so that its solubility properties overcome the insolubility of the aniline moiety(ies). For example, when one monomer (e.g., $-CH_2CH_2O-$) is included in the polyethylene glycol chain (i.e., n=1 in formulas I), the polymeric amine synergist is minimally water soluble, and as the number of monomers increases, the water solubility of the polymeric amine synergist increases. In addition, water soluble R groups can be included or added to the aniline moiety(ies) to increase the solubility of the polymeric amine synergist. In one example, the polymeric amine synergist can have a water solubility of at least 0.05 wt %. When the water solubility is at least 0.05 wt %, it means that of the total wt % of the polymeric amine synergist added to water, at least 0.05 wt % of the total is water soluble. In another example, the water solubility of the polymeric amine synergist is at least 0.5 wt %. In some instances, the polymeric amine synergist may have a water solubility up to about 100 wt %.

Typical aqueous ink jet inks can have a pH in the range of 7 to 14. Some commercially available synergists with ester linkages can break down in such basic conditions. However, the polymeric amine synergists disclosed herein can be stable under these conditions. In some examples, the polymeric amine synergist can be stable in a water based composition having a pH ranging from 7 to 14. In other examples, the polymeric amine synergist can be stable in a water based composition having a pH of 8 or higher. As used herein, the term "stable" refers to the ability of the polymeric amine synergist to have a shelf life of at least 1 year. As examples, the aqueous ink jet inks disclosed herein can have a shelf life of greater than 1 year, greater than 2 years, or longer.

An example of a pathway for forming an example of the polymeric amine synergist disclosed herein (e.g., the example shown in formula I) is shown in scheme (V):

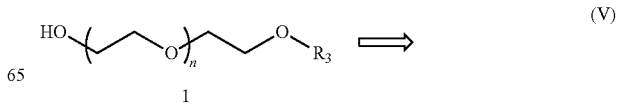

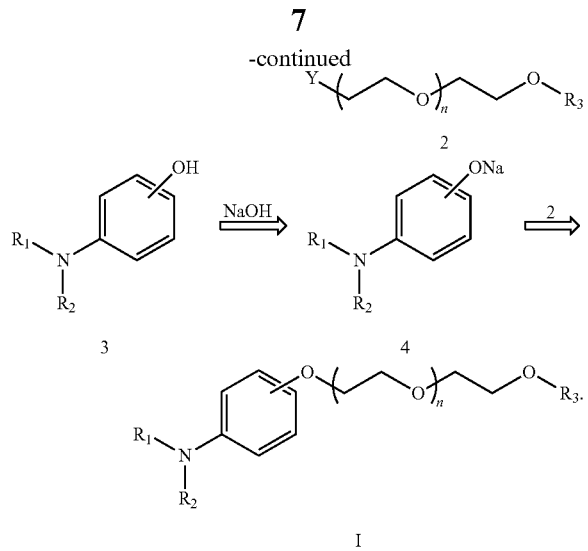

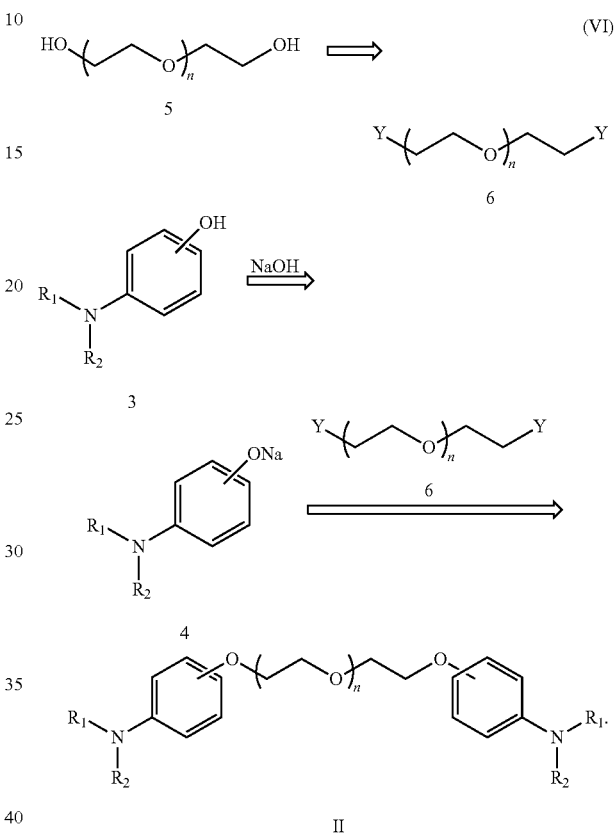

In scheme (V), "1" represents the polyethylene glycol chain starting material, and "3" represents the aniline moiety starting material. In these starting materials, $R_1$, $R_2$ and $R_3$ are each independently selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, a substituted or unsubstituted aralkyl group, a halogen atom, $—NO_2$, $—O—R_d$, $—CO—R_d$, $—CO—O—R_d$, $—O—CO—R_d$, $—CO—NR_dR_e$, $—NR_dR_e$, $—NR_d—CO—R_e$, $—NR_d—CO—O—R_e$, $—NR_d—CO—NR_eR_f$, $—SR_d$, $—SO—R_d$, $—SO_2—R_d$, $—SO_2—O—R_d$, $—SO_2NR_dR_e$ and a perfluoroalkyl group. $R_d$, $R_e$, and $R_f$ are each independently selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, and a substituted or unsubstituted aralkyl group. As mentioned above, some examples of suitable alkyl groups include methyl, ethyl, propyl, isopropyl, butyl, isobutyl, pentyl, hexyl, etc.; one example of a suitable alkene group is an ethylene group; and some examples of suitable aryl groups include phenyl, phenylmethyl, etc. The letter n in starting material 1 ranges from 1 to 200.

In scheme (V), the polyethylene glycol chain starting material 1 is a mono-substituted polyethylene glycol ether. It is to be understood that other polyethylene glycol chain starting materials 1 may be used. The polyethylene glycol chain starting material 1 is reacted with a leaving group reagent to form a leaving group modified polyethylene glycol ether (shown as "2"). The leaving group reagent may include any leaving group, denoted Y. In an example, Y may be chlorine (Cl), bromine (Br), iodine (I), a tosylate group (OTs), or a triflate group (trifluoromethanesulfonate or OTf).

In scheme (V), the aniline moiety starting material 3 may be dimethylaminophenol. It is to be understood that other aniline moiety starting materials 3 may be used. The aniline moiety starting material 3 is treated with sodium hydroxide (or another suitable hydroxide, e.g., KOH) to produce the corresponding sodium salt (shown as "4").

A substitution reaction between the sodium salt 4 and the leaving group modified polyethylene glycol ether 2 under reflux produces the polymeric amine synergist having formula I. As previously stated herein, the polyethylene glycol chain of formula I may be connected to different positions of the benzene ring (e.g., the para or meta positions), depending upon the aniline moiety starting material 3 that is used.

Another example of a pathway for forming another example of the polymeric amine synergist disclosed herein (e.g., the example shown in formula II) may be formed as shown in scheme (VI):

In scheme (VI), "5" represents the polyethylene glycol chain starting material, and "3" represents the aniline moiety starting material. In the aniline moiety starting material 3, $R_1$ and $R_2$ may be any of the groups previously described herein. In the polyethylene glycol chain starting material 5, n ranges from 1 to 200.

In scheme (VI), the polyethylene glycol chain starting material 5 is polyethylene glycol ether. It is to be understood that other polyethylene glycol chain starting materials 5 may be used. The polyethylene glycol chain starting material 5 is reacted with a leaving group reagent to form a leaving group modified polyethylene glycol ether (shown as "6"). The leaving group reagent may include any leaving group Y, such as chlorine (Cl), bromine (Br), iodine (I), a tosylate group (OTs), or a triflate group (trifluoromethanesulfonate or OTf).

In scheme (VI), the aniline moiety starting material 3 may be dimethylaminophenol. It is to be understood that other aniline moiety starting materials 3 may be used. The aniline moiety starting material 3 is treated with sodium hydroxide (or another suitable hydroxide) to produce the corresponding sodium salt 4.

A substitution reaction between the sodium salt 4 and the leaving group modified polyethylene glycol ether 6 under reflux produces the polymeric amine synergist having formula II. It is to be understood that the polyethylene glycol chain of formula II may be connected to different positions of the first benzene ring (e.g., the para or meta positions) and the ethylene glycol unit of formula II may be connected to different positions of the second benzene ring (e.g., the para or meta positions), depending upon the aniline moiety starting material 3 that is used.

Yet another example of a pathway for forming an example of the polymeric amine synergist disclosed herein (e.g., the example shown in formula III) may be formed as shown in scheme (VII):

In scheme (VII), "7" represents the polyethylene glycol chain starting material, and "3" represents the aniline moiety starting material. In these starting materials 7 and 3, $R_1$, $R_2$ and $R_3$ may be any of the groups previously described herein. Each letter n in starting material 7 ranges from 1 to 200.

In scheme (VII), the polyethylene glycol chain starting material 7 is a glycerol polyethylene glycol derivative. It is to be understood that other polyethylene glycol chain starting materials 7 may be used. The polyethylene glycol chain starting material 7 is reacted with a leaving group reagent to form a leaving group modified compound (shown as "8"). The leaving group reagent may include any leaving group Y previously described.

In scheme (VII), the aniline moiety starting material 3 may be dimethylaminophenol. It is to be understood that other aniline moiety starting materials 3 may be used. The aniline moiety starting material 3 is treated with sodium hydroxide (or another suitable hydroxide) to produce the corresponding sodium salt 4.

A substitution reaction between the sodium salt 4 and the leaving group modified compound 8 under reflux produces the polymeric amine synergist having formula III. As previously stated herein, the first, second, and third polyethylene glycol chains may be connected to different positions of the respective first, second, and third benzene rings (e.g., the para or meta positions), depending upon the aniline moiety starting material 3 that is used.

Still a further example of a pathway for forming still another example of the polymeric amine synergist disclosed herein (e.g., the example shown in formula IV) may be formed as shown in scheme (VIII):

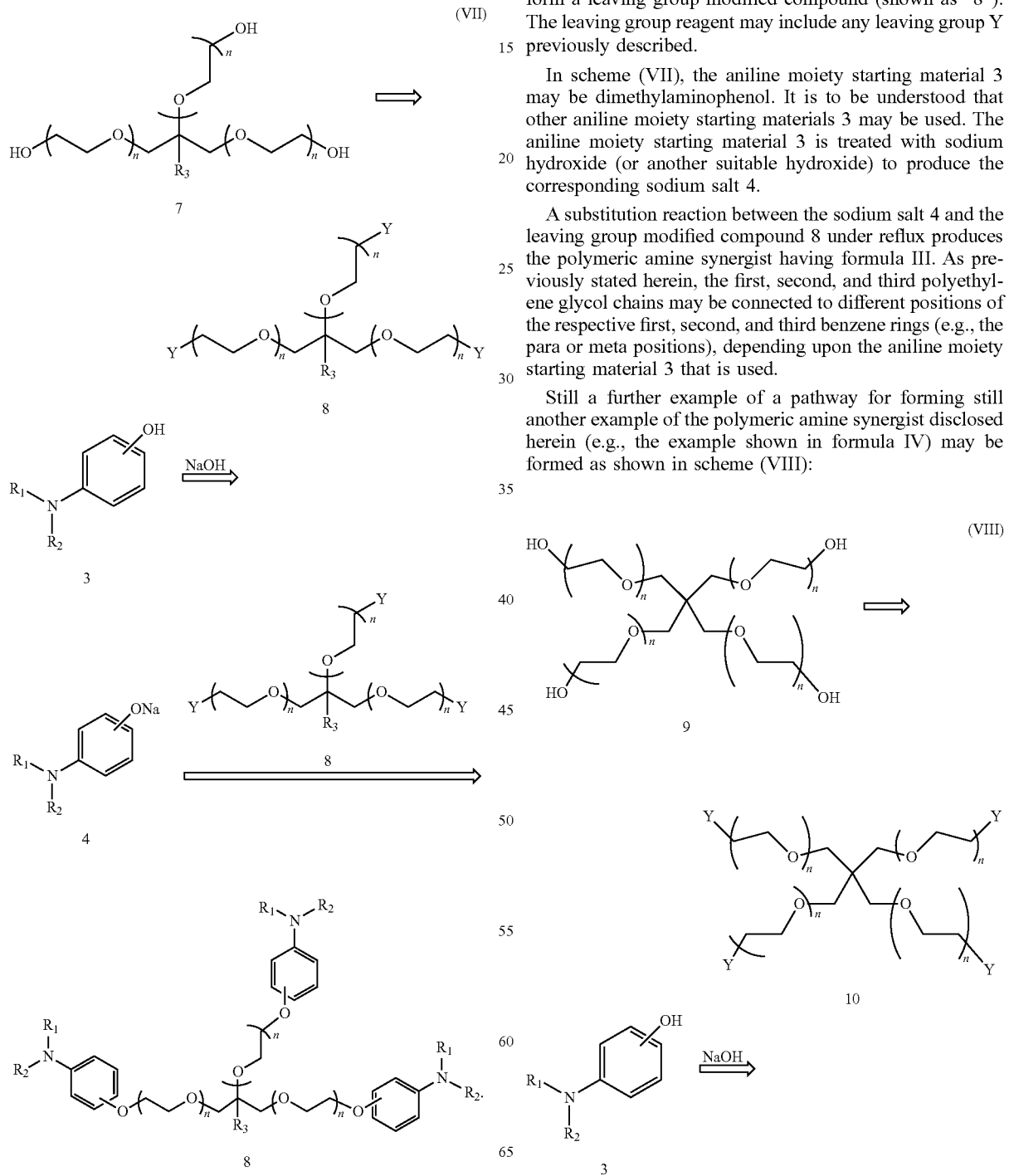

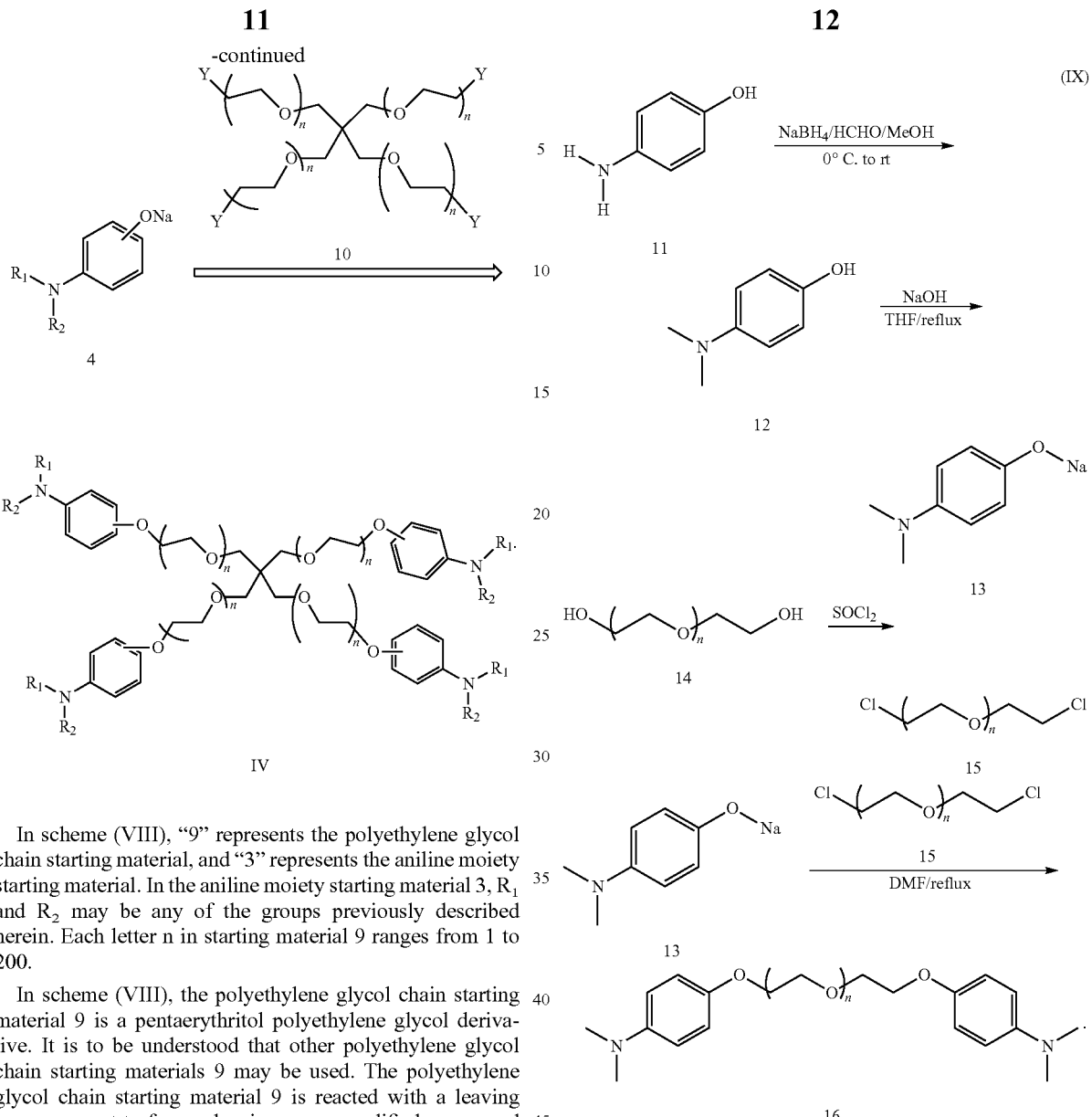

In scheme (VIII), "9" represents the polyethylene glycol chain starting material, and "3" represents the aniline moiety starting material. In the aniline moiety starting material 3, $R_1$ and $R_2$ may be any of the groups previously described herein. Each letter n in starting material 9 ranges from 1 to 200.

In scheme (VIII), the polyethylene glycol chain starting material 9 is a pentaerythritol polyethylene glycol derivative. It is to be understood that other polyethylene glycol chain starting materials 9 may be used. The polyethylene glycol chain starting material 9 is reacted with a leaving group reagent to form a leaving group modified compound (shown as "10"). The leaving group reagent may include any leaving group Y previously described.

In scheme (VIII), the aniline moiety starting material 3 may be dimethylaminophenol. It is to be understood that other aniline moiety starting materials 3 may be used. The aniline moiety starting material 3 is treated with sodium hydroxide (or another suitable hydroxide) to produce the corresponding sodium salt 4.

A substitution reaction between the sodium salt 4 and the leaving group modified compound 10 under reflux produces the polymeric amine synergist having formula IV. As previously stated herein, the first, second, third and fourth polyethylene glycol chains may be connected to different positions of the respective first, second, third, and fourth benzene rings (e.g., the para or meta positions), depending upon the aniline moiety starting material 3 that is used.

The following schemes provide more detailed examples of the pathways for forming examples of the polymeric amine synergist disclosed herein. One example pathway is shown in scheme (IX):

In scheme IX, the aniline moiety starting material is 4-aminophenol (shown as "11"). 4-aminophenol 11 is reacted with sodium borohydride and formaldehyde in methanol to produce 4-dimethylaminophenol (shown as "12"). This reaction may take place at a temperature ranging from about 0° C. to room temperature (rt, generally ranging from about 18° C. to about 22° C.). The treatment of 4-dimethylaminophenol 12 with sodium hydroxide in tetrahydrofuran (THF) under reflux forms the corresponding sodium salt 13.

Concurrently or subsequently, a reaction between the polyethylene glycol starting material 14 (in this example PEG) and thionyl chloride ($SOCl_2$) is performed to produce dichloro-polyethylene glycol (shown as "15"). The substitution reaction between the sodium salt 13 and dichloro-polyethylene glycol 15 forms the polymeric amine synergist 16 (one example of the synergist with formula II). As previously stated herein, the polyethylene glycol chain of synergist 16 may be connected to different positions of the first benzene ring (e.g., the para or meta positions) and the ethylene glycol unit of synergist 16 may be connected to different positions of the second benzene ring (e.g., the para or meta positions), depending upon the aniline moiety starting material 3 that is used.

Another example pathway for forming the synergist 16 is shown in scheme (X):

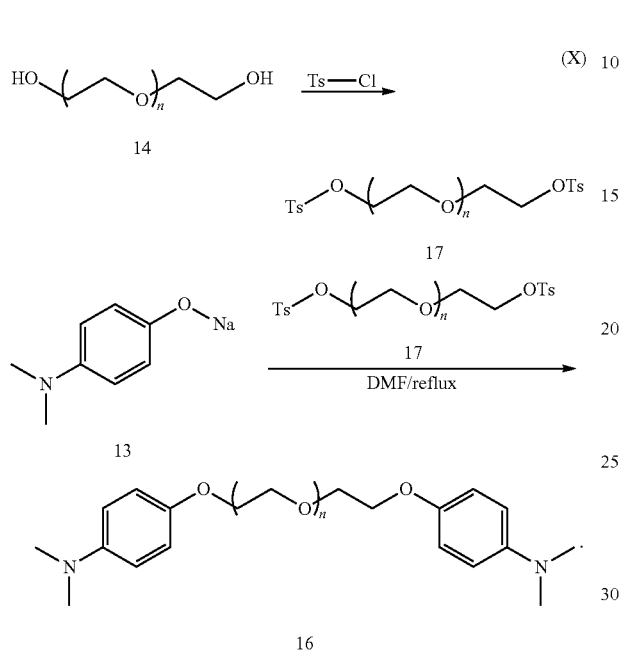

In scheme X, the polyethylene glycol 14 is reacted with toluenesulfonyl chloride (Ts-Cl) to form polyethylene glycol di-tosylate (shown as "17").

While not shown in scheme X, the treatment of 4-dimethylaminophenol (12 in scheme IX) with sodium hydroxide in tetrahydrofuran (THF) under reflux forms the corresponding sodium salt 13.

A substitution reaction of the sodium salt 13 with polyethylene glycol di-tosylate 17 in dimethylformamide (DMF) under reflux forms the polymeric amine synergist 16. As previously stated herein, the polyethylene glycol chain of synergist 16 may be connected to different positions of the first benzene ring (e.g., the para or meta positions) and the ethylene glycol unit of synergist 16 may be connected to different positions of the second benzene ring (e.g., the para or meta positions), depending upon the aniline moiety starting material 3 that is used.

Another more detailed pathway for forming an example synergist with one analine moiety is shown in scheme (XI):

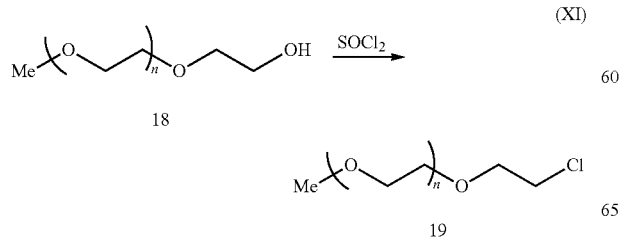

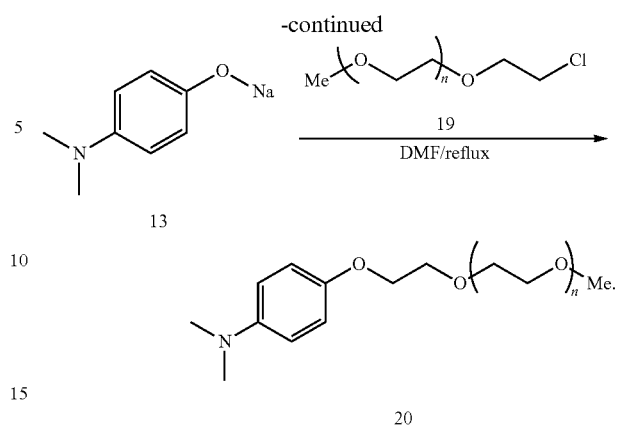

In scheme XI, the reaction between mono-methyl substituted polyethylene glycol 18 (the polyethylene glycol starting material) and thionyl chloride (SOCl$_2$) forms chloro mono-methyl substituted polyethylene glycol (shown as "19").

While not shown in scheme XI, the treatment of 4-dimethylaminophenol (12 in scheme IX) with sodium hydroxide in tetrahydrofuran (THF) under reflux forms the corresponding sodium salt 13.

A substitution reaction of the sodium salt 13 and the chloro mono-methyl substituted polyethylene glycol 19 produces the polymeric amine synergist 20. In this example synergist, the ether linkage includes an ethylene glycol monomer unit which attaches the oxygen atom of the ether linkage to one end of the polyethylene glycol chain. As previously stated herein, the polyethylene glycol chain may be connected to different positions of the benzene ring (e.g., the para or meta positions), depending upon the aniline moiety starting material 3 that is used.

Another example pathway for forming the synergist 20 is shown in scheme (XII):

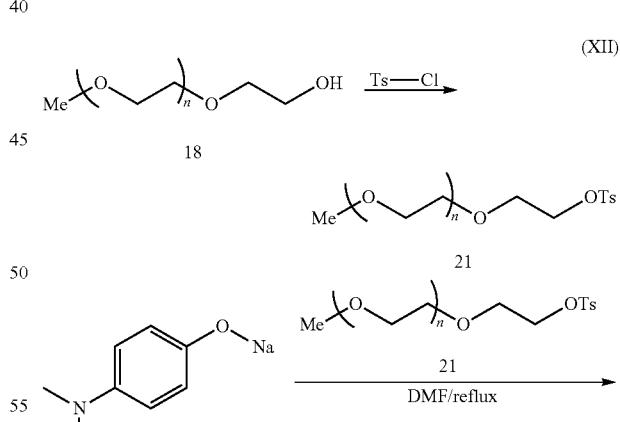

In scheme XII, a reaction between mono-methyl substituted polyethylene glycol 18 and toluenesulfonyl chloride (Ts-Cl) forms mono-methyl substituted polyethylene glycol tosylate (shown as "21").

While not shown in scheme XII, the treatment of 4-dimethylaminophenol (12 in scheme IX) with sodium hydroxide in tetrahydrofuran (THF) under reflux forms the corresponding sodium salt 13.

A substitution reaction of the sodium salt (13) and the mono-methyl substituted polyethylene glycol tosylate 21 produces the polymeric amine synergist 20. As previously stated herein, the polyethylene glycol chain may be connected to different positions of the benzene ring (e.g., the para or meta positions), depending upon the aniline moiety starting material 3 that is used.

The present disclosure also extends to photo curable inks/ink compositions, such as UV curable inks including light emitting diode ("LED") curable inks. In some examples, the photo curable ink composition can include a photo-reactive binder (such as a UV curable or LED curable binder), a type-II photoinitiator, an example of the polymeric amine synergist disclosed herein, a colorant, a co-solvent, and a balance of water. It is to be understood that the polymeric amine synergist may be any of the example polymeric amine synergists disclosed herein.

In some examples, the photo-reactive binder can include a combination of a UV or LED curable polyurethane and hydrophobic radiation-curable monomer(s). In one example, the photo-reactive binder can include a water dispersible (meth)acrylated polyurethane, such as NEORAD® R-441 by NeoResins (Avecia). Other examples of UV reactive binders can include UCECOAT® 7710, UCECOAT® 7655 (available from Cytec), NEORAD® R-440, NEORAD® R-441, NEORAD® R-447, NEORAD® R-448 (available from DSM NeoResins), BAYHYDROL® UV 2317, BAYHYDROL® UV VP LS 2348 (available from Bayer), Lux 430, Lux 399, Lux 484 (available from Alberdingk Boley), LAROMER® LR 8949, LAROMER® LR 8983, LAROMER® PE 22WN, LAROMER® PE 55WN, or LAROMER® UA 9060 (available from BASF).

The polymeric amine synergists of the present disclosure can be used together with a type-II photo initiator. The combination of the type-II photoinitiator with the polymeric amine synergist can interact by hydrogen abstraction. In this interaction, UV radiation causes a hydrogen radical to be abstracted from the polymeric amine synergist onto the type-II photo initiator. This creates two molecules having radicals that can initiate polymerization in the photo-reactive binder. The polymeric amine synergist may be the main free radical that initiates polymerization.

In some cases, the photo curable ink composition can include two different photoinitiators, or a photoinitiator and a sensitizer. Some examples of type-II photoinitiators can also act as sensitizers. In one example, the photo curable ink composition may include a polymeric photoinitiator that includes a xanthone analog, such as thioxanthone, connected to a polyether chain. In another example, the xanthone analog can connect to the polyether chain through an ether linkage or an amide linkage. These types of photoinitiators can act either as a type-II photoinitiator or as a sensitizer. The photo curable ink composition can also include other polymeric or non-polymeric photoinitiators. Examples of radical photoinitiator that may be used include 1-hydroxycyclohexylphenylketone, benzophenone, 2,4,6-trimethylbenzophenone, 4-methylbenzophenone, diphenyl-(2,4,6-trimethylbenzoyl)phosphine oxide, phenyl bis(2,4,6-trimethylbenzoyl)phosphine oxide, 2-hydroxy-2-methyl-1-phenyl-1-propanone (i.e., 2-hydroxy-2methylpropiohphenone), benzyl-dimethyl ketal, 2-methyl-1-[4-(methylthio)phenyl]-2-morpholino propan-1-one, or combinations thereof. Examples of additional photoinitiators that may be used include alpha amino ketone UV photo initiators, such as IRGACURE® 907, IRGACURE® 369, and IRGACURE® 379 (BASF Corp.); bis acylphosphine oxide (BAPO) UV photo initiators, such as IRGACURE® 819, DAROCUR® 4265, and DAROCUR® TPO (BASF Corp.); alpha hydroxy ketone UV photo initiators, such as IRGACURE® 184 and DAROCUR® 1173 (BASF Corp.); and photoinitiators with or without sensitizers, such as DAROCUR® ITX (2-isopropyl thioxanthone) (BASF Corp.).

The photoinitiator and the polymeric amine synergist disclosed herein may each independently be present in the photo curable ink composition in an amount ranging from about 0.1% to about 25% by weight based on the total wt % of the photo curable ink composition. In another example, each of the photoinitiator and the polymeric amine synergist may be present in an amount ranging from about 0.25% to about 10% by weight. In still another example, each of the photoinitiator and polymeric amine synergist may be present in an amount ranging from about 0.25% to about 5% by weight. The amount of photoinitiator may be the same as or different from the amount of the polymeric amine synergist.

The colorant in the photo curable ink composition may be a pigment or a dye. In some examples, the colorant can be present in an amount from about 0.5 wt % to about 10 wt % based on a total wt % of the photo curable ink composition. In one example, the colorant can be present in an amount from about 1 wt % to about 5 wt %. In another example, the colorant can be present in an amount from about 5 wt % to about 10 wt %.

In some examples, the colorant may be a dye. As used herein, "dye" refers to compounds or molecules that absorb electromagnetic radiation or certain wavelengths thereof. Dyes can impart a visible color to the ink composition if the dyes absorb wavelengths in the visible spectrum. The dye can be nonionic, cationic, anionic, or a mixture of nonionic, cationic, and/or anionic dyes. Specific examples of dyes that may be used include Sulforhodamine B, Acid Blue 113, Acid Blue 29, Acid Red 4, Rose Bengal, Acid Yellow 17, Acid Yellow 29, Acid Yellow 42, Acridine Yellow G, Acid Yellow 23, Acid Blue 9, Nitro Blue Tetrazolium Chloride Monohydrate or Nitro BT, Rhodamine 6G, Rhodamine 123, Rhodamine B, Rhodamine B Isocyanate, Safranine O, Azure B, and Azure B Eosinate, which are available from Sigma-Aldrich Chemical Company (St. Louis, Mo.). Examples of anionic, water-soluble dyes include Direct Yellow 132, Direct Blue 199, Magenta 377 (available from Ilford AG, Switzerland), alone or together with Acid Red 52. Examples of water-insoluble dyes include azo, xanthene, methine, polymethine, and anthraquinone dyes. Specific examples of water-insoluble dyes include ORASOL® Blue GN, ORASOL® Pink, and ORASOL® Yellow dyes available from BASF Corp. Black dyes may include Direct Black 154, Direct Black 168, Fast Black 2, Direct Black 171, Direct Black 19, Acid Black 1, Acid Black 191, Mobay Black SP, and Acid Black 2.

In other examples, the colorant may be a pigment. As used herein, "pigment" generally includes pigment colorants, magnetic particles, aluminas, silicas, and/or other ceramics, organo-metallics or other opaque particles, whether or not such particulates impart color. Thus, although the present description primarily illustrates the use of pigment colorants, the term "pigment" can be used more generally to describe pigment colorants, as well as other pigments such as organometallics, ferrites, ceramics, etc. In one specific example, however, the pigment is a pigment colorant.

The pigment can be self-dispersed with a polymer, an oligomer, or a small molecule; or it can be dispersed with a separate dispersant. Suitable pigments include the following, which are available from BASF Corp.: PALIOGEN® Orange, HELIOGEN® Blue L 6901F, HELIOGEN® Blue NBD 7010, HELIOGEN® Blue K 7090, HELIOGEN® Blue L 7101F, PALIOGEN® Blue L 6470, HELIOGEN® Green K 8683, HELIOGEN® Green L 9140, CHROMOPHTAL® Yellow 3G, CHROMOPHTAL® Yellow GR, CHROMOPHTAL® Yellow 8G, IGRAZIN® Yellow 5GT, and IGRALITE® Rubine 4BL. The following black pigments are available from Cabot Corp.: MONARCH® 1400, MONARCH® 1300, MONARCH® 1100, MONARCH® 1000, MONARCH® 900, MONARCH® 880, MONARCH® 800, and MONARCH® 700. The following pigments are available from Orion Engineered Carbons GMBH: PRINTEX® U, PRINTEX® V, PRINTEX® 140U, PRINTEX® 140V, Color Black FW 200, Color Black FW 2, Color Black FW 2V, Color Black FW 1, Color Black FW 18, Color Black S 160, Color Black S 170, Special Black 6, Special Black 5, Special Black 4A, and Special Black 4. The following pigment is available from DuPont: TI-PURE® R-101. The following pigments are available from Heubach: MONASTRAL® Magenta, MONASTRAL® Scarlet, MONASTRAL® Violet R, MONASTRAL® Red B, and MONASTRAL® Violet Maroon B. The following pigments are available from Clariant: DALAMAR® Yellow YT-858-D, Permanent Yellow GR, Permanent Yellow G, Permanent Yellow DHG, Permanent Yellow NCG-71, Permanent Yellow GG, Hansa Yellow RA, Hansa Brilliant Yellow 5GX-02, Hansa Yellow-X, NOVOPERM® Yellow HR, NOVOPERM® Yellow FGL, Hansa Brilliant Yellow 10GX, Permanent Yellow G3R-01, HOSTAPERM® Yellow H4G, HOSTAPERM® Yellow H3G, HOSTAPERM® Orange GR, HOSTAPERM® Scarlet GO, and Permanent Rubine F6B. The following pigments are available from Sun Chemical: QUINDO® Magenta, INDOFAST® Brilliant Scarlet, QUINDO® Red R6700, QUINDO® Red R6713, INDOFAST® Violet, L74-1357 Yellow, L75-1331 Yellow, L75-2577 Yellow, and LHD9303 Black. The following pigments are available from Birla Carbon: RAVEN® 7000, RAVEN® 5750, RAVEN® 5250, RAVEN® 5000, and RAVEN® 3500. The colorant may be a white pigment, such as titanium dioxide, or other inorganic pigments such as zinc oxide and iron oxide.

Any other pigment or dye can be used that is useful in modifying the color of the UV curable ink.

The components of the photo curable ink composition can be selected to provide the ink composition with a suitable ink jetting performance. Besides the photo curable binder, the polymeric amine synergist, the photoinitiator(s), and the colorant, the photo curable ink composition can also include a liquid vehicle. Liquid vehicle formulations that can be used in the photo curable ink composition can include water and co-solvent(s) present in a total amount ranging from about 1 wt % to about 50 wt % based on the total wt % of the photo curable ink composition. The total amount and type of co-solvent(s) may also depend on the jetting architecture.

Classes of co-solvents that may be used can include organic co-solvents, including aliphatic alcohols, aromatic alcohols, diols, glycol ethers, polyglycol ethers, caprolactams, formamides, acetamides, and long chain alcohols. Examples of such compounds include primary aliphatic alcohols, secondary aliphatic alcohols, 1,2-alcohols, 1,3-alcohols, 1,5-alcohols, ethylene glycol alkyl ethers, propylene glycol alkyl ethers, higher homologs (C6-C12) of polyethylene glycol alkyl ethers, N-alkyl caprolactams, unsubstituted caprolactams, both substituted and unsubstituted formamides, both substituted and unsubstituted acetamides, and the like. Specific examples of co-solvents that can be used include 2-pyrrolidinone, N-methylpyrrolidone, 2-hydroxyethyl-2-pyrrolidone, 2-methyl-1,3-propanediol, tetraethylene glycol, 1,6-hexanediol, 1,5-hexanediol and 1,5-pentanediol.

Further, a dispersant, such as a non-ionic, cationic, anionic, and/or amphoteric surfactant, can be present in the liquid vehicle, in an amount ranging from about 0 wt % to about 20 wt % based on the total wt % of the photo curable ink composition. In one example, the dispersant/surfactant can be present in an amount from about 0.01 wt % to about 20 wt %. In another example, the dispersant surfactant can be present in an amount from about 5 wt % to about 20 wt %. In still another example, the dispersant surfactant can be present in an amount up to 10 wt %. In one example, the dispersant is a combination of an anionic surfactant and a non-ionic surfactant.

Examples of suitable dispersants/surfactants include alkyl polyethylene oxides, alkyl phenyl polyethylene oxides, polyethylene oxide block copolymers, acetylenic polyethylene oxides, polyethylene oxide (di)esters, protonated polyethylene oxide amines, protonated polyethylene oxide amides, dimethicone copolyols, substituted amine oxides, and the like. Suitable surfactants can include liponic esters such as TERGITOL™ 15-S-12, Tergitol™ 15-S-7 (available from Dow Chemical Company), LEG-1, and LEG-7; a nonionic, octylphenol ethoxylate surfactant, such as TRITON™ X-100 or TRITON™ X-405 available from Dow Chemical Company; and sodium dodecylsulfate.

Some examples of the anionic surfactant may include alkylbenzene sulfonate, alkylphenyl sulfonate, alkylnaphthalene sulfonate, a higher fatty acid salt, a sulfate ester salt of higher fatty acid ester, a sulfonate of higher fatty acid ester, a sulfate ester salt and sulfonate of higher alcohol ether, higher alkyl sulfosuccinate, polyoxyethylene alkylether carboxylate, polyoxyethylene alkylether sulfate, alkyl phosphate, and polyoxyethylene alkyl ether phosphate. Some specific examples of the anionic surfactant include dodecylbenzenesulfonate, isopropylnaphthalenesulfonate, monobutylphenylphenol monosulfonate, monobutylbiphenyl sulfonate, and dibutylphenylphenol disulfonate.

Some examples of the nonionic surfactant may include polyoxyethylene alkyl ether, polyoxyethylene alkyl phenyl ether, polyoxyethylene fatty acid ester, sorbitan fatty acid ester, polyoxyethylene sorbitan fatty acid ester, polyoxyethylene sorbitol fatty acid ester, glycerin fatty acid ester, polyoxyethylene glycerin fatty acid ester, polyglycerin fatty acid ester, sucrose fatty acid ester, polyoxyethylene alkylamine, polyoxyethylene fatty acid amide, alkyl alkanolamide, fatty acid alkyloamide, polyethylene glycol polypropylene glycol block copolymer, acetylene glycol, and a polyoxyethylene adduct of acetylene glycol. Some specific examples of the nonionic surfactant include polyoxyethylenenonyl phenylether, polyoxyethyleneoctyl phenylether, and polyoxyethylenedodecyl phenylether. Further examples of the nonionic surfactant may include silicon surfactants, such as a polysiloxane oxyethylene adduct; fluorine surfactants, such as perfluoroalkylcarboxylate, perfluoroalkyl sulfonate, and oxyethyleneperfluoro alkylether; and biosurfactants, such as spiculisporic acid, rhamnolipid, and lysolecithin.

The balance of the liquid vehicle and the ink composition can be purified water.

The ink composition may also include various other additives to enhance the properties of the ink composition for specific applications. Examples of these additives include those added to inhibit the growth of harmful microorganisms, viscosity modifiers, materials for pH adjustment, sequestering agents, anti-kogation agents, preservatives, and the like.

The additives added to inhibit the growth of harmful microorganisms may be biocides, fungicides, and other microbial agents, which are routinely used in ink formulations. Examples of suitable microbial agents include, but are not limited to, NUOSEPT® (Nudex, Inc.), UCARCIDE™ (Union carbide Corp.), VANCIDE® (R.T. Vanderbilt Co.), PROXEL® (ICI America), and combinations thereof.

Sequestering agents, such as EDTA (ethylene diamine tetra acetic acid), may be included to eliminate the deleterious effects of heavy metal impurities, and buffer solutions may be used to control the pH of the ink. From about 0.01 wt % to about 2 wt % of the sequestering agent and/or the buffer solution, for example, can be used. Viscosity modifiers may also be present, as well as other additives to modify properties of the ink as desired. Such additives can be present in an amount ranging from about 0.01 wt % to about 20 wt % based on the total wt % of the ink composition.

Table 1 shows the composition of an example of the photo curable ink composition (e.g. UV or LED curable) in accordance with the present disclosure. The ink can be formulated by mixing these ingredients or by other formulation techniques. The pH of the ink can then be adjusted. In one example, the ingredients can be stirred for 30 minutes, and then aqueous potassium hydroxide can be added to adjust the pH to 8.5. It is noted that although the water concentration is listed as the balance, the balance of the ink composition could include other liquid vehicle components or minor amounts of solids often present in inkjet ink compositions.

TABLE 1

| Component | Weight Percent |
|---|---|
| Photo-reactive binder | 1-20% |
| Type-II Photoinitiator | 0.15-5% |
| Co-photo initiator | 0-10% |
| Polymeric amine synergist | 0.1-5% |
| Surfactant | 0-20% |
| Anti-kogation agent | 0.1-5% |
| Pigment or Dye | 0.5-10% |
| Organic Co-solvent | 0.1-50% |
| Water | balance |

The photo curable ink composition can be printed on a broad selection of substrates, including untreated plastics, flexible as well as rigid, porous substrates such as paper, cardboard, foam board, textile, and others. The ink composition exhibits good adhesion on a variety of substrates. The photo curable ink composition also has viscosity suitable for inkjet printing, thus enabling good printing performance. In some examples, the ink composition can be formulated for thermal inkjet printing. The photo-curable ink composition of the present disclosure enables high printing speed and is very well suited for use in digital inkjet printing.

The polymeric amine synergists of the present disclosure can be stable in aqueous environments at pH from 7 to 14 or higher. Thus, the photo curable ink composition can be formulated to have a pH from 7 to 14 or higher. In some examples, the photo curable ink can have a pH of 8 or higher. In one specific example, the photo curable ink can have a pH of 8.5.

As mentioned herein, the polymeric amine synergist can exhibit less migration in the cured ink compared with small molecule synergists. The photo curable binder in the ink composition can include polymers or monomers that polymerize or cross-link during the curing process. As the binder cures, the polymeric amine synergist can become locked into the cured binder due, in part, to the long polyethylene glycol chain of the polymeric amine synergist. Therefore, there is little or no migration of the polymeric amine synergist in the cured ink composition.

The present disclosure also extends to a method of making the photo curable ink composition. In an example, a method can include mixing the reactive binder, the photoinitiator, an example of the polymeric amine synergist disclosed herein, the colorant, and the liquid vehicle, which includes at least co-solvent(s) and water. In one example, the method can also include adjusting the pH of the ink composition to be from 7 to 14. In another example, the method can include adjusting the pH of the ink to be 8 or higher.

The photo curable ink composition can be UV curable, and in one specific example, may be UV LED curable. As used herein, "UV curable" refers to compositions that can be cured by exposure to ultraviolet light from any UV source such as a mercury vapor lamp, UV LED source, or the like. Mercury vapor lamps emit high intensity light at wavelengths from 240 nm to 270 nm and 350 nm to 380 nm. "LED curable" refers to compositions that can be cured by ultraviolet light from an ultraviolet LED. Ultraviolet LEDs typically emit light at specific wavelengths. For example, ultraviolet LEDs are available at 365 nm and 395 nm wavelengths, among others. The term "photo curable" refers generally to compositions that can be cured by exposure to light from any wavelength suitable for the composition being cured. Typically, the photo curable composition will be UV curable, and in some cases UV LED curable.

To further illustrate the present disclosure, examples are given herein. It is to be understood that these examples are provided for illustrative purposes and are not to be construed as limiting the scope of the present disclosure.

EXAMPLES

Example 1—Synthesis of 4-Dimethylaminophenol (Component 12 in Scheme IX)

In this example, a solution including 54.65 g (0.5 mol) of 4-aminophenol in 600 mL of methanol was added to 90 g (3.0 mol) of formaldehyde at room temperature. The solution was cooled to −5° C. using a salted ice bath. The solution was then slowly added, portion wise, to 113.5 g (3.0 mol) of sodium borohydride to form a mixture. After the completion of the addition of sodium borohydride, the mixture was stirred at room temperature for 24 hours. Then, the reaction was quenched via the addition of ice-water and organic material was extracted with chloroform (3 times, 100 mL each). As noted, the extraction was performed 3 times, and the organic material was combined to form an organic layer. The organic layer was dried over sodium sulfate. The sodium sulfate was removed by filtration and the solvent was evaporated in a vacuum. The residue was further purified by flash chromatography, providing 56.3 g of the final product of 4-dimethylaminophenol (82% yield).

Example 2—Synthesis of the Sodium Salt 4-Dimethylaminophenol (Component 13 in Scheme IX)

In this example, a solution including 17.16 g (0.125 mol) of 4-dimethylaminophenol in 100 mL of tetrahydrofuran (THF) was added to 30 g (0.75 mol) of sodium hydroxide to form a mixture in a flask. The mixture was heated to reflux for 2 hours. After cooling the mixture down to room temperature, the THF was evaporated. Then, 500 mL of water was added to the flask and stirred for 3 hours. The solid was separated by filtration, washed with water (2 times, 200 mL each), acetone (2 times, 100 mL each), and then hexane (2 times, 100 mL each). The solid was then dried in an oven overnight to produce 18 g of the sodium salt of 4-dimethylaminophenol (90% yield).

Example 3—Synthesis of Dichloro-Polyethylene Glycol-600 (Component 15 in Scheme IX)

For this example, a mixture including 100 g (0.1 mol) of polyethylene glycol-600, 60 g (0.5 mol) of thionyl chloride, and 0.1 g of N-dimethylformamide (DMF) was heated to reflux for 5 hours. After cooling the mixture down to room temperature, 20 mL of methanol was added slowly to the mixture and stirred for 1 hour. Then, the methanol and unreacted thionyl chloride were removed by vacuum to produce 102 g of dichloro-polyethylene glycol (96% yield).

Example 4—Synthesis of Polyethylene Glycol Di-Tosylate (Component 17 in Scheme X)

In this example, a solution including 100 g (0.167 mol) of polyethylene glycol-600 in 250 mL of dichloromethane was added to 14 mL (0.16 mol) of pyridine. The solution was cooled to 0° C. and then 22.88 g (0.12 mol) of p-toluenesulfonyl chloride was added portion-wise at 0° C. in an inert environment ($N_2$ gas). The resulting solution was poured into ice-water. The organic layer was separated, and the aqueous layer was extracted with chloroform (2 times, 50 mL each). As noted, the separation and extraction was performed 2 times, and the organic layers were combined. The combined organic layer was washed with water and dried over sodium sulfate. The sodium sulfate was filtered and the evaporation of the solvent left 128 g of polyethylene glycol di-tosylate (85% yield).

Example 5—Synthesis of Chloro Mono-Methyl Polyethylene Glycol Ether (Component 19 in Scheme XI)

For this example, a mixture including 100 g (0.18 mol) of mono-methyl polyethylene glycol ether, 60 g (0.5 mol) of thionyl chloride, and 0.1 g of N-dimethylformamide (DMF) was heated to reflux for 5 hours. After cooling down to room temperature, 20 mL of methanol was added slowly to the solution and stirred for 1 hour. Then, the methanol and unreacted thionyl chloride were removed by vacuum to form 100 g of chloro mono-methyl polyethylene glycol ether (97% yield).

Example 6—Synthesis of Mono-Methyl Polyethylene Glycol Ether Tosylate (Component 22 in Scheme XII)

In this example, 28 mL (0.32 mol) of pyridine was added to a solution including 100 g (0.182 mol) of mono-methyl polyethylene glycol ether 550 in 250 mL of dichloromethane. The solution was cooled to 0° C. and then 34.89 g (0.183 mol) of p-toluenesulfonyl chloride was added portion-wise at 0° C. in an inert environment ($N_2$ gas). The resulting solution was poured into ice-water. The organic layer was separated, and the aqueous layer was extracted with chloroform (2 times, 50 mL each). As noted, the separation and extraction was performed 2 times, and the organic layers were combined. The combined organic layer was washed with water and dried over sodium sulfate. The sodium sulfate was filtered and the evaporation of the solvent produced 115 g of mono-methyl polyethylene glycol tosylate (90% yield).

Example 7—Synthesis of Bis(4-Dimethylaminophenol) Derivative of PEG 600 (Component 16 in Scheme IX) from Dichloride In this example, a mixture including 7.95 g (50 mmol) of sodium salt of 4-dimethylaminophenol and 15.93 g (25 mmol) of dichloro-polyethylene glycol-600 in 50 mL of N-dimethylformamide (DMF) was heated to reflux for 2 hours. Then, the DMF was removed by distillation. After cooling down to room temperature, the residue was added to 500 mL of acetone and 10 g of activated carbon. The mixture was then heated to reflux for 20 min. Then, the solid was filtered by filtration. Evaporation of the solvent using a rotary evaporator produced a residue, which was further purified by flash chromatography. 31 g of bis(4-dimethylaminophenol) derivative of PEG 600 was obtained (75% yield).

Example 8—Synthesis of Bis(4-Dimethylaminophenol) Derivative of PEG 600 (Component 16 in Scheme X) from Ditosylate In this example, a mixture including 7.95 g (50 mmol) of sodium salt of 4-dimethylaminophenol and 22.55 g (25 mmol) of polyethylene glycol-600 di-tosylate in 50 mL of N-dimethylformamide (DMF) was heated to reflux for 2 hours. Then, the DMF was removed by distillation. After cooling down to room temperature, the residue was added to 500 mL of acetone and 10 grams of activated carbon. The mixture was then heated to reflux for 20 min. Then, the solid was filtered by filtration. Evaporation of the solvent using a rotary evaporator gave a residue, which was further purified by flash chromatography. 36 g of bis(4-dimethylaminophenol) derivative of PEG 600 was obtained (85% yield).

Example 9—Synthesis of Mono-(4-Dimethylaminophenol) Derivative of PEG 550 (Component 20 in Scheme XI) from Chloride In this example, a mixture including 7.95 g (50 mmol) of sodium salt of 4-dimethylaminophenol and 28.43 g (50 mmol) of chloro mono-methyl polyethylene glycol ether in 50 mL of N-dimethylformamide (DMF) was heated to reflux for 2 hours. Then, the DMF was removed by distillation. After cooling down to room temperature, the residue was added to 500 mL of acetone and 10 grams of activated carbon. The mixture was then heated to reflux for 20 min. Then, the solid was filtered by filtration. Evaporation of the solvent using a rotary evaporator gave a residue, which was further purified by flash chromatography. 28.5 g of mono-(4-dimethylaminophenol) derivative of PEG 550 was obtained (85% yield).

Example 10—Synthesis of Mono-(4-Dimethylaminophenol) Derivative of PEG 550 (Component 20 in Scheme XII) from Tosylate In this example, a mixture of 7.95 g (50 mmol) of sodium salt of 4-dimethylaminophenol and 35.05 g (50 mmol) of mono-methyl polyethylene glycol ether 550 tosylate in 50 mL of N-dimethylformamide (DMF) was heated to reflux for 2 hours. Then, the DMF was removed by distillation. After cooling down to room temperature, the residue was added to 500 mL of acetone and 10 grams of activated carbon. The mixture was then heated to reflux for 20 min. Then, the solid was filtered by filtration. Evaporation of the solvent using a rotary evaporator gave a residue, which was further purified by flash chromatography. 30.1 g of mono-(4-dimethylaminophenol) derivative of PEG 550 was obtained (90% yield).

Example 11—Synthesis of Photo Curable Inkjet Ink Compositions

Each photo curable inkjet ink composition formulated in this Example was prepared by mixing a first solution including the total amount of ultraviolet polyurethane dispersion (UV-PUD) and co-photointiator used in the photo curable inkjet ink composition (amounts shown in the Tables below) with 30% of the total amount of water used in the photo curable inkjet ink composition. The first solution was mixed at 60° C. for 5 minutes. A second solution was prepared by mixing the total amount of co-solvent, anti-kogation agent, and surfactants used in the ink composition (amounts shown in the Tables below) with 70% of the total amount of water used in the photo curable inkjet ink composition. The second solution was neutralized to a pH of about 7.5 with potassium hydroxide solution (KOH). The solutions were then combined. The type-II photoinitiator and the polymeric amine synergist were added to the combined solution and mixed until each component dissolved. This combined solution was then added to a pigment dispersion and the pH was adjusted to 8.5 using the KOH solution to from the example photo curable inkjet inks listed below.

The examples of the photo curable inkjet ink composition are shown in the Tables below:

Example Ink 1

| Component | Weight Percent |
| --- | --- |
| UV polyurethane binder | 15% |
| IRGACURE ® 819 (co-photo initiator) | 0.3% |
| Thioxanthone derivative of PEG-600 (type-II photo initiator) | 0.5% |
| mono-(4-dimethylaminophenol) derivative of mono-methyl polyethylene glycol ether 550 (polymeric amine synergist) | 0.5% |
| LEG-1 (surfactant) | 1% |
| SURFYNOL ® CT-211 (surfactant) | 1% |
| CRODAFOS ® N3 (anti-kogation agent) | 0.5% |
| Pigment solids | 2.5% |
| 1,2-hydroxyethyl-2-pyrrolidone (co-solvent) | 10% |
| Water | 69.2% |

Example Ink 2

| Component | Weight Percent |
| --- | --- |
| UV polyurethane binder | 5% |
| Thioxanthone derivative of PEG-600 (type-II photo initiator) | 0.25% |
| bis-(4-dimethylaminophenol) derivative of polyethylene glycol-600 (polymeric amine synergist) | 0.5% |
| LEG-1 (surfactant) | 1% |
| SURFYNOL ® CT-211 (surfactant) | 0.5% |
| CRODAFOS ® N3 (anti-kogation agent) | 0.5% |
| Pigment solids | 3% |
| 1,2-hydroxyethyl-2-pyrrolidone (co-solvent) | 10% |
| Water | 79.15% |

Example Ink 3

| Component | Weight Percent |
| --- | --- |
| UV polyurethane binder | 10% |
| Thioxanthone derivative of PEG-600 (type-II photo initiator) | 0.25% |
| bis-(4-dimethylaminophenol) derivative of polyethylene glycol-600 (polymeric amine synergist) | 0.5% |
| LEG-1 (surfactant) | 1% |
| SURFYNOL ® CT-211 (surfactant) | 0.5% |
| CRODAFOS ® N3 (anti-kogation agent) | 0.5% |
| Pigment solids | 3% |
| 1,2-hydroxyethyl-2-pyrrolidone (co-solvent) | 10% |
| Water | 74.15% |

Example Ink 4

| Component | Weight Percent |
| --- | --- |
| UV polyurethane binder | 15% |
| Irgacure ® 819 (co-photo initiator) | 0.3% |
| Thioxanthone derivative of PEG-600 (type-II photo initiator) | 0.5% |
| bis-(4-dimethylaminophenol) derivative of polyethylene glycol-600 (polymeric amine synergist) | 1% |
| LEG-1 (surfactant) | 1% |
| SURFYNOL ® CT-211 (surfactant) | 1% |
| CRODAFOS ® N3 (anti-kogation agent) | 0.5% |
| Pigment solids | 2.5% |
| 1,2-hydroxyethyl-2-pyrrolidone (co-solvent) | 10% |
| Water | 68.7% |

Example Ink 5

| Component | Weight Percent |
| --- | --- |
| UV polyurethane binder | 15% |
| Irgacure ® 819 (co-photo initiator) | 0.3% |
| Thioxanthone derivative of PEG-600 (type-II photo initiator) | 0.5% |
| bis-(4-dimethylaminophenol) derivative of polyethylene glycol-600 (polymeric amine synergist) | 3% |
| LEG-1 (surfactant) | 1% |
| SURFYNOL ® CT-211 (surfactant) | 1% |

-continued

| Component | Weight Percent |
|---|---|
| CRODAFOS ® N3 (anti-kogation agent) | 0.5% |
| Pigment solids | 2.5% |
| 1,2-hydroxyethyl-2-pyrrolidone (co-solvent) | 10% |
| Water | 66.7% |

Example Ink 6

| Component | Weight Percent |
|---|---|
| UV polyurethane binder | 15% |
| Irgacure ® 819 (co-photo initiator) | 0.3% |
| Thioxanthone derivative of PEG-600 (type-II photo initiator) | 0.5% |
| bis-(4-dimethylaminophenol) derivative of polyethylene glycol-600 (polymeric amine synergist) | 5% |
| LEG-1 (surfactant) | 1% |
| SURFYNOL ® CT-211 (surfactant) | 1% |
| CRODAFOS ® N3 (anti-kogation agent) | 0.5% |
| Pigment solids | 2.5% |
| 1,2-hydroxyethyl-2-pyrrolidone (co-solvent) | 10% |
| Water | 64.7% |

Example ink 1 was filled into a thermal inkjet pen (TIJ4). A fixer was printed from a different inkjet pen prior to the printing of Example ink1. The fixer and Example ink 1 were printed onto Sterling Ultra Gloss media (SUG) and Whitetop coated Kraft liner RockTenn 1 media (RT1). Example ink 1 was dried using a hot air blower for 5 seconds at a temperature of 375° F. Some examples of the dried Example ink 1 were then cured at a speed of 100 feet per minute (fpm) using a 16 W/cm$^2$ light emitting diode (LED) (available from Phoseon) at a wavelength of 395 nm.

After Example ink 1 was printed, a wet rub test and an immediate rub test were performed. Also, after Example ink 1 was printed and cured, the wet rub test and the immediate rub test were performed.

For the print on the SUG media, the wet rub test was performed 24 hours after printing or printing and curing. For the print on the RT1 media, the wet rub test was performed 72 hours after printing or printing and curing. The wet rub test was performed using a Taber test tool with a Crockmeier cloth attached to the tip. The weight load was 350 g (grams). The Example ink 1 prints on SUG media was subjected to 1 cycle and the Example ink 1 prints on the RT1 media was subjected to 2 cycles. A WINDEX® solution was applied to the prints before applying the weight load. The change in optical density (ΔOD) was calculated using the before and after optical density measurements. The ΔOD results are also shown below in Table 2.

The immediate rub test was performed immediately on each media after printing and after printing and curing of the Example ink 1. This test assessed the smearing of the dried or the dried and cured ink. The immediate rub test was performed using a hand held rubbing tool fit with a rubber tip that when pushed on the media applied a constant pressure of 6 lbs to 7 lbs. The optical density was measured before and after the immediate rub test was performed. The ΔOD was calculated using the before and after optical density measurements. The ΔOD results are also shown below in Table 2.

TABLE 2

| Example 1 Ink - delta OD (ΔOD) | After Printing and Curing | | After Printing | |
|---|---|---|---|---|
| | Wet Rub | Immediate Rub | Wet Rub | Immediate Rub |
| SUG media | 0.20 | 0.15 | 1.93 | 0.85 |
| RT1 media | 0.11 | 0.08 | 1.34 | 0.65 |

The results show that Example ink 1 has significantly better wet rub and immediate rub resistance after curing. A ΔOD of 0.20 for cured Example ink 1 after the wet rub test on SUG media indicates that after the rub tests, the print lost 0.20 OD units on SUG media compared to the initial OD. In contrast, the wet rub test on SUG media of Example ink 1 without curing resulted in a ΔOD of 1.93. This indicates that the print lost 1.93 OD units compared to the initial OD measurement. The significant loss in optical density is evidence that the uncured ink is not durable.

The reduced optical density loss, and thus durability improvement, of Example 1 ink after curing is evident in both the wet rub and the immediate rub test. The results demonstrate that the type-II photoinitiator and the polymeric amine synergist disclosed herein are effectively curing and crosslinking the ink to form a durable printed image.

It is to be understood that the ranges provided herein include the stated range and any value or sub-range within the stated range. For example, a range from about 0.1 wt % to about 5 wt % should be interpreted to include not only the explicitly recited limits of about 0.1 wt % to about 5 wt %, but also to include individual values, such as 1.3 wt %, 2.5 wt %, 4.5 wt %, etc., and sub-ranges, such as from about 2 wt % to about 4 wt %, from about 3.2 wt % to about 4.3 wt %, etc. Furthermore, when "about" is utilized to describe a value, this is meant to encompass minor variations (up to +/−10%) from the stated value.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

In describing and claiming the examples disclosed herein, the singular forms "a", "an", and "the" include plural referents unless the context clearly dictates otherwise.

While several examples have been described in detail, it is to be understood that the disclosed examples may be modified. Therefore, the foregoing description is to be considered non-limiting.

What is claimed is:

1. A polymeric amine synergist, comprising:
   an aniline moiety;
   a polyethylene glycol chain; and
   an ether linkage attaching one end of the polyethylene glycol chain to the aniline moiety.

2. The polymeric amine synergist as defined in claim 1 wherein:
the polymeric amine synergist has a formula of:

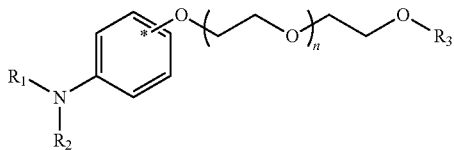

$R_1$, $R_2$ and $R_3$ are each independently selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, a substituted or unsubstituted aralkyl group, a halogen atom, —$NO_2$, —O—$R_d$, —CO—$R_d$, —CO—O—$R_d$, —O—CO—$R_d$, —CO—$NR_dR_e$, —$NR_dR_e$, —$NR_d$—CO—$R_e$, —$NR_d$—CO—O—$R_e$, —$NR_d$—CO—$NR_eR_f$, —$SR_d$, —SO—$R_d$, —$SO_2$—$R_d$, —$SO_2$—O—$R_d$, —$SO_2NR_dR_e$ and a perfluoroalkyl group;

$R_d$, $R_e$, and $R_f$ are each independently selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, and a substituted or unsubstituted aralkyl group; and n ranges from 1 to 200.

3. The polymeric amine synergist as defined in claim 1, further comprising an additional aniline moiety attached to an opposed end of the polyethylene glycol chain through an additional ether linkage.

4. The polymeric amine synergist as defined in claim 3 wherein:
the polymeric amine synergist has a formula of:

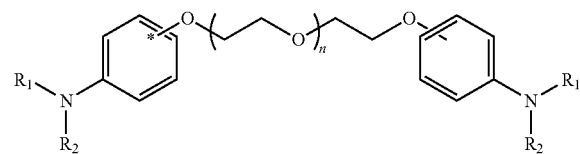

$R_1$ and $R_2$ are each independently selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, a substituted or unsubstituted aralkyl group, a halogen atom, —$NO_2$, —O—$R_d$, —CO—$R_d$, —CO—O—$R_d$, —O—CO—$R_d$, —CO—$NR_dR_e$, —$NR_dR_e$, —$NR_d$—CO—$R_e$, —$NR_d$—CO—O—$R_e$, —$NR_d$—CO—$NR_eR_f$, —$SR_d$, —SO—$R_d$, —$SO_2$—$R_d$, —$SO_2$—O—$R_d$, —$SO_2NR_dR_e$ and a perfluoroalkyl group;

$R_d$, $R_e$, and $R_f$ are each independently selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, and a substituted or unsubstituted aralkyl group; and n ranges from 1 to 200.

5. The polymeric amine synergist as defined in claim 1 wherein:
the polyethylene glycol chain is a first polyethylene glycol chain;
the polymeric amine synergist further comprises:
second and third polyethylene glycol chains; and
second and third aniline moieties;
the second polyethylene glycol chain is attached to an opposed end of the first polyethylene glycol chain and the second aniline moiety is attached to the second polyethylene glycol chain through a second ether linkage; and
the third polyethylene glycol chain is attached to the opposed end of the first polyethylene glycol chain and the third aniline moiety is attached to the third polyethylene glycol chain through a third ether linkage.

6. The polymeric amine synergist as defined in claim 5 wherein:
the polymeric amine synergist has a formula of:

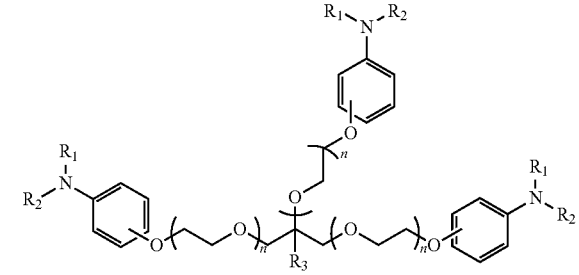

$R_1$, $R_2$ and $R_3$ are each independently selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, a substituted or unsubstituted aralkyl group, a halogen atom, —$NO_2$, —O—$R_d$, —CO—$R_d$, —CO—O—$R_d$, —O—CO—$R_d$, —CO—$NR_dR_e$, —$NR_dR_e$, —$NR_d$—CO—$R_e$, —$NR_d$—CO—O—$R_e$, —$NR_d$—CO—$NR_eR_f$, —$SR_d$, —SO—$R_d$, —$SO_2$—$R_d$, —$SO_2$—O—$R_d$, —$SO_2NR_dR_e$ and a perfluoroalkyl group;

$R_d$, $R_e$, and $R_f$ are each independently selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, and a substituted or unsubstituted aralkyl group; and n ranges from 1 to 200.

7. The polymer amine synergist as defined in claim 5, further comprising:
a fourth polyethylene glycol chain attached to the opposed end of the first polyethylene glycol chain; and
a fourth aniline moiety attached to the fourth polyethylene glycol chain through a fourth ether linkage.

8. The polymeric amine synergist as defined in claim 7 wherein:

the polymeric amine synergist has a formula of:

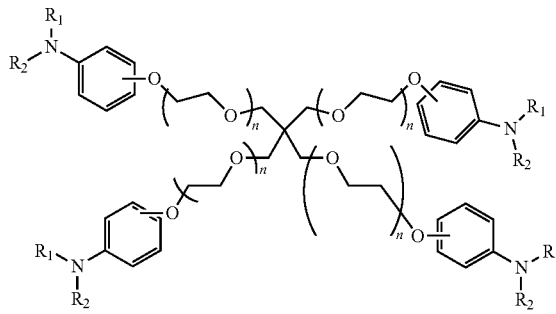

R$_1$ and R$_2$ are each independently selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, a substituted or unsubstituted aralkyl group, a halogen atom, —NO$_2$, —O—R$_d$, —CO—R$_d$, —CO—O—R$_d$, —O—CO—R$_d$, —CO—NR$_d$R$_e$, —NR$_d$R$_e$, —NR$_d$—CO—R$_e$, —NR$_d$—CO—O—R$_e$, —NR$_d$—CO—NR$_e$R$_f$, —SR$_d$, —SO—R$_d$, —SO$_2$—R$_d$, —SO$_2$—O—R$_d$, —SO$_2$NR$_d$R$_e$ and a perfluoroalkyl group;

R$_d$, R$_e$, and R$_f$ are each independently selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, and a substituted or unsubstituted aralkyl group; and n ranges from 1 to 200.

9. The polymeric amine synergist as defined in claim 1 wherein the polymeric amine synergist is stable in water at a pH ranging from about 7 to about 14.

10. The polymeric amine synergist as defined in claim 1 wherein the polymeric amine synergist has a water solubility of at least 0.05 wt %.

11. A photo curable ink composition, comprising:
a photo-reactive binder;
a polymeric amine synergist, including:
 an aniline moiety;
 a polyethylene glycol chain; and
 an ether linkage attaching one end of the polyethylene glycol chain to the aniline moiety;
a type-II photoinitiator;
a colorant;
a co-solvent; and
a balance of water.

12. The photo curable ink composition as defined in claim 11 wherein:
the polymeric amine synergist has a formula selected from the group consisting of:

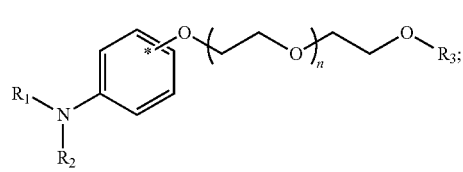

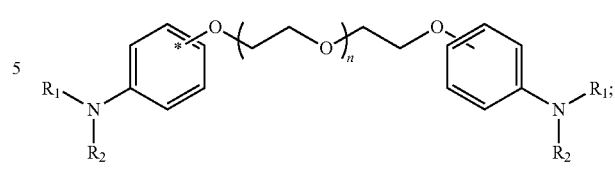

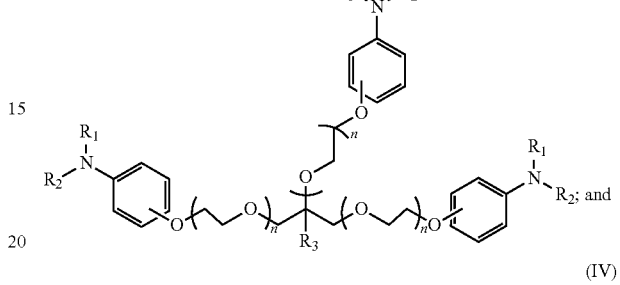

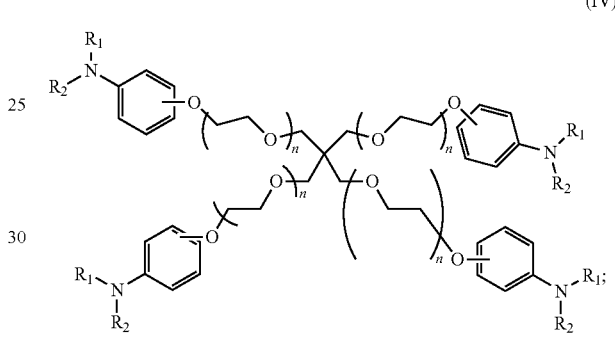

any of R$_1$, R$_2$ or R$_3$ is selected from the group consisting of a hydrogen atom, a substituted or unsubstituted alkyl group, a substituted or unsubstituted allyl group, a substituted or unsubstituted alkene group, a substituted or unsubstituted alkenyl group, a substituted or unsubstituted aryl group, a substituted or unsubstituted aralkyl group, a halogen atom, —NO$_2$, —O—R$_d$, —CO—R$_d$, —CO—O—R$_d$, —O—CO—R$_d$, —CO—NR$_d$R$_e$, —NR$_d$R$_e$, —NR$_d$—CO—R$_e$, —NR$_d$—CO—O—R$_e$, —NR$_d$—CO—NR$_e$R$_f$, —SR$_d$, —SO—R$_d$, —SO$_2$—R$_d$, —SO$_2$—O—R$_d$, —SO$_2$NR$_d$R$_e$ and a perfluoroalkyl group;

R$_d$, R$_e$, and R$_f$ are each independently selected from the group consisting of a hydrogen atom, a substituted or unsubstituted alkyl group, a substituted or unsubstituted alkenyl group, a substituted or unsubstituted aryl group, and a substituted or unsubstituted aralkyl group; and n ranges from 1 to 200.

13. The photo curable ink composition as defined in claim 11 wherein the polymeric amine synergist does not migrate in the photo curable ink composition after curing.

14. The photo curable ink composition as defined in claim 11 wherein the polymeric amine synergist is present in the photo curable ink composition in an amount ranging from about 0.1 wt % to about 5 wt % based on a total wt % of the photo curable ink composition.

15. A method of making a photo curable ink, comprising:
obtaining a polymeric amine synergist, including:
 an aniline moiety;
 a polyethylene glycol chain; and an ether linkage attaching one end of the polyethylene glycol chain to the aniline moiety; and mixing the polymeric amine synergist with a photo-reactive binder, a type-II photo initiator, a colorant, a co-solvent, and a balance of water.

* * * * *